United States Patent
Kuwae et al.

(10) Patent No.: US 10,779,717 B2
(45) Date of Patent: Sep. 22, 2020

(54) ENDOSCOPE

(71) Applicant: FUJIFILM Corporation, Tokyo (JP)

(72) Inventors: Toshiharu Kuwae, Kanagawa (JP); Takeshi Yukiiri, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 251 days.

(21) Appl. No.: 15/135,519

(22) Filed: Apr. 21, 2016

(65) Prior Publication Data

US 2016/0309994 A1 Oct. 27, 2016

(30) Foreign Application Priority Data

Apr. 24, 2015 (JP) ................. 2015-089678

(51) Int. Cl.
*A61B 1/12* (2006.01)
*A61B 1/00* (2006.01)
*A61B 1/015* (2006.01)

(52) U.S. Cl.
CPC .......... *A61B 1/126* (2013.01); *A61B 1/00091* (2013.01); *A61B 1/015* (2013.01); *A61B 1/12* (2013.01)

(58) Field of Classification Search
CPC ... A61B 1/126; A61B 1/00091; A61B 1/0008; A61B 1/00096; A61B 1/12; A61B 1/127; A61B 1/128; A61B 1/00119; A61B 1/00163; A61B 1/00165; A61B 1/00174; A61B 1/00177; A61B 1/00179; A61B 1/00181; A61B 1/00183; A61B 1/00186;
(Continued)

(56) References Cited

U.S. PATENT DOCUMENTS 7,896,802 B2 3/2011 Otawara
2007/0135682 A1* 6/2007 Miyagi .............. A61B 1/00094
600/129

(Continued)

FOREIGN PATENT DOCUMENTS

CN 101098655 1/2008
JP 2007209395 A * 8/2007 ......... A61B 1/00091
(Continued)

OTHER PUBLICATIONS

Otawara, English translation of JP2007209395A attached (Year: 2007).*

(Continued)

*Primary Examiner* — Ryan N Henderson
*Assistant Examiner* — Pamela F Wu
(74) *Attorney, Agent, or Firm* — JCIPRNET

(57) ABSTRACT

Cleaning performance or wiping performance for an observation window is improved in an endoscope. In a distal end face of a distal end part of the endoscope, a guide part rising to a distal end side is provided between an observation window and a fluid injection nozzle. A width of the guide face of the guide part has a narrowed part, and a portion with the narrowest width serves as a fluid guiding part. The fluid guiding part guides fluid passing through a position of the fluid guiding part, in fluid injected from the fluid injection nozzle, to a first fluid route through which the fluid is guided to the observation window. Fluid deviated from the fluid guiding part is guided to a region adjacent to the observation window through a second fluid route.

5 Claims, 10 Drawing Sheets

(58) Field of Classification Search
CPC ... A61B 1/00188; A61B 1/0019; A61B 1/015; A61B 1/04–06; A61B 1/0661; A61B 1/0669; A61B 1/0676; A61B 1/0684; A61B 1/07
USPC .......... 600/156–180, 109, 129, 153
See application file for complete search history.

(56) References Cited

U.S. PATENT DOCUMENTS

| | | | | |
|---|---|---|---|---|
| 2007/0260118 | A1* | 11/2007 | Otawara | A61B 1/0008 600/129 |
| 2008/0064928 | A1* | 3/2008 | Otawara | A61B 1/00091 600/129 |
| 2011/0112363 | A1* | 5/2011 | Koga | A61B 1/05 600/109 |
| 2011/0306838 | A1* | 12/2011 | Ikeda | A61B 1/00091 600/157 |
| 2012/0226104 | A1 | 9/2012 | Ikeda et al. | |
| 2014/0058204 | A1 | 2/2014 | Ikeda et al. | |
| 2014/0094659 | A1 | 4/2014 | Hamazaki et al. | |
| 2017/0049308 | A1 | 2/2017 | Ikeda et al. | |

FOREIGN PATENT DOCUMENTS

| | | |
|---|---|---|
| JP | 2010200944 | 9/2010 |
| JP | 2012179221 | 9/2012 |
| WO | 2014030385 | 2/2014 |

OTHER PUBLICATIONS

"Notice of Allowance of Japan Counterpart Application," with machine English translation thereof, dated Jun. 18, 2018, p. 1-p. 6.
Office Action of China Counterpart Application, with English translation thereof, dated Nov. 1, 2018, pp. 1-19.
"Office Action of Japan Counterpart Application," with machine English translation thereof, dated Apr. 24, 2018, p. 1-p. 8.

* cited by examiner

ENDOSCOPE

CROSS-REFERENCE TO RELATED APPLICATIONS

The present application claims priority under 35 U.S.C. § 119 to Japanese Patent Application No. 2015-089678, filed on Apr. 24, 2015. The above application is hereby expressly incorporated by reference, in its entirety, into the present application.

BACKGROUND OF THE INVENTION

Field of the Invention

The present invention relates to an endoscope, and more particularly to an endoscope with improved cleaning performance for an observation window at a distal end part of an insertion section.

Description of the Related Art

In a distal end face at a distal end part of an insertion section of an endoscope, there are provided an observation window for receiving a subject light from an observation target site, and an illumination window for emitting illumination light to the observation target site. The distal end face is provided with a fluid injection nozzle (air-supply/water-supply nozzle) that injects fluid of cleaning liquid (such as water) or gas (such as air) to the observation window to remove accretions, such as body fluid, adhering to the observation window.

When the observation window is cleaned, first the fluid injection nozzle injects cleaning liquid to remove accretions, such as body fluid, adhering to the observation window, and subsequently, the fluid injection nozzle injects gas to remove the cleaning liquid remaining on the observation window.

International Publication No. WO 2014/030385 provides cleaning of this kind of observation window in which a tapered inclined part is formed in a peripheral part of the observation window to allow a fluid injected from a fluid injection nozzle to spread throughout a surface of the observation window, thereby improving cleaning performance for the entire surface of the observation window, as well as wiping performance of removing cleaning liquid.

Unfortunately, even if the gas injected from the fluid injection nozzle after the cleaning liquid is injected removes the cleaning liquid from the entire surface of the observation window, some cleaning liquid may remain in a region adjacent to the observation window. At this time, the cleaning liquid may cause a phenomenon, such as halation or limb darkening, on an observation image to deteriorate image quality of the observation image.

Heretofore, the fluid injected from a fluid injection nozzle is attempted to be spread over an entire surface of an observation window, as described in International Publication No. WO 2014/030385, however, the cleaning liquid may remain in a region adjacent to the observation window. As a result, it may take a long time to remove the cleaning liquid to the extent that the image quality of an observation image is not affected.

Particularly, in the case of structure in which the illumination window is arranged near the observation window, the cleaning liquid tends to remain between the observation window and the illumination window, and thus removal of the cleaning liquid may be prolonged.

The present invention is made in light of the above-mentioned circumstances, and it is an object to provide an endoscope in which a fluid injected from a fluid injection nozzle can reliably flow to an observation window and a region adjacent to the observation window and cleaning performance or wiping performance for the observation window is improved.

SUMMARY OF THE INVENTION

To achieve the object above, an endoscope in accordance with one aspect of the present invention includes: an insertion section having a distal end, a proximal end, and a longitudinal axis; an operation section provided at the proximal end of the insertion section; a distal end face provided at the distal end of the insertion section; an observation window arranged in the distal end face; a fluid injection nozzle arranged in the distal end face, the fluid injection nozzle configured to inject a fluid to the observation window; a fluid guiding part that is provided at a position between the fluid injection nozzle and the observation window, the fluid guiding part having a width less than an opening width of the fluid injection nozzle in a direction orthogonal to a straight line connecting a center of the fluid injection nozzle and a center of the observation window, the fluid guiding part configured to guide a part of the fluid injected from the fluid injection nozzle to an observation window side; a first fluid route having a first guide face configured to guide the part of the fluid guided by the fluid guiding part to the observation window, the first guide face being formed of a continuous face connecting between the fluid guiding part and the observation window; and a second fluid route having a second guide face configured to guide a fluid deviated from the fluid guiding part in the fluid injected from fluid injection nozzle to a region adjacent to the observation window, the second guide face being formed of a face including a step projecting to a distal end side of the insertion section in a direction of the longitudinal axis larger on an observation window side than on a fluid injection nozzle side, the step having a component obliquely intersecting with the straight line connecting the center of the fluid injection nozzle and the center of the observation window when the distal end face is viewed from a front in the direction of the longitudinal axis.

According to the present aspect, the fluid guiding part is arranged between the fluid injection nozzle and the observation window, and a fluid passing through the fluid guiding part is guided to the first fluid route in which the fluid is guided to the observation window, and a fluid deviated from the fluid guiding part is guided to the second fluid route in which the fluid is guided to the region adjacent to the observation window. As a result, changing the width of the fluid guiding part enables to adjust a ratio between the fluid to be guided to the first fluid route and the fluid to be guided to the second fluid route. Then, when the width of the fluid guiding part is set less than the opening width of the fluid injection nozzle, the fluid to be guided to the second fluid route can be reliably secured, in the fluid injected from the fluid injection nozzle so as to enable the fluid to be reliably supplied to the region adjacent to the observation window.

Thus, when gas is injected after a cleaning liquid is injected from the fluid injection nozzle, the cleaning liquid can be reliably and rapidly removed from a surface region of the observation window as well as the region adjacent to the observation window.

In an endoscope in accordance with another aspect of the present invention, the distal end face may include a fluid holding region in the region adjacent to the observation window.

According to the present aspect, the cleaning liquid is positively held in the fluid holding region in the region adjacent to the observation window, and thus the gas guided to the second fluid route can reliably blow away the cleaning liquid in the fluid holding region.

In an endoscope in accordance with yet another aspect of the present invention, the fluid holding region may have a surface energy higher than a surface energy of a surface of the observation window.

In an endoscope in accordance with yet another aspect of the present invention, the distal end face may include a recessed part in the region adjacent to the observation window, and the recessed part constitutes the fluid holding region.

In an endoscope in accordance with yet another aspect of the present invention, the first guide face may be composed of a first inclined surface configured to incline to the distal end side of the insertion section in the direction of the longitudinal axis from the fluid guiding part to the observation window.

In an endoscope in accordance with yet another aspect of the present invention, the first guide face may be composed of a second inclined surface configured to incline to a proximal end side of the insertion section in the direction of the longitudinal axis from the fluid guiding part toward the observation window.

An endoscope in accordance with yet another aspect of the present invention may include a third guide face provided between the fluid injection nozzle and the fluid guiding part, and the third guide face may include a third inclined surface configured to incline to the proximal end side of the insertion section as a distance from the fluid injection nozzle increases.

In an endoscope in accordance with yet another aspect of the present invention, the second guide face may include a face parallel to an optical axis of the observation window.

In addition, to achieve the object above, an endoscope in accordance with yet another aspect of the present invention includes: an insertion section having a distal end, a proximal end, and a longitudinal axis; an operation section provided at the proximal end of the insertion section; a distal end face provided at the distal end of the insertion section; an observation window arranged in the distal end face; a fluid injection nozzle arranged in the distal end face, the fluid injection nozzle configured to inject a fluid to the observation window; a fluid guiding part that is provided at a position between the fluid injection nozzle and the observation window, the fluid guiding part having a width less than an opening width of the fluid injection nozzle in a direction orthogonal to a straight line connecting a center of the fluid injection nozzle and a center of the observation window, the fluid guiding part configured to guide a part of the fluid injected from the fluid injection nozzle to an observation window side; a first fluid route having a first guide face configured to guide the part of the fluid guided by the fluid guiding part to the observation window, the first guide face being formed of a continuous face connecting between the fluid guiding part and the observation window; and a second fluid route having a second guide face configured to guide a fluid deviated from the fluid guiding part in the fluid injected from fluid injection nozzle to a region adjacent to the observation window, the second guide face being formed of a face including a step projecting to a distal end side of the insertion section in a direction of the longitudinal axis larger on an observation window side than on a fluid injection nozzle side, the step having a component obliquely intersecting with the straight line connecting the center of the fluid injection nozzle and the center of the observation window when the distal end face is viewed from a front in the direction of the longitudinal axis, wherein when it is assumed that the straight line connecting the center of the fluid injection nozzle and the center of the observation window is a first straight line, and a line orthogonal to the first straight line and an optical axis of the observation window is a second straight line, the first guide face is composed of only a face parallel to the second straight line.

According to the present aspect, the fluid guiding part is arranged between the fluid injection nozzle and the observation window, and a fluid passing through the fluid guiding part is guided to the first fluid route in which the fluid is guided to the observation window, and a fluid deviated from the fluid guiding part is guided to the second fluid route in which the fluid is guided to the region adjacent to the observation window. As a result, changing the width of the fluid guiding part enables to adjust a ratio between the fluid to be guided to the first fluid route and the fluid to be guided to the second fluid route. Then, when the width of the fluid guiding part is set less than the opening width of the fluid injection nozzle, the fluid to be guided to the second fluid route can be reliably secured in the fluid injected from the fluid injection nozzle so as to enable the fluid to be reliably supplied to the region adjacent to the observation window.

Thus, when gas is injected after a cleaning liquid is injected from the fluid injection nozzle, the cleaning liquid can be reliably and rapidly removed from the surface region of the observation window as well as the region adjacent to the observation window.

The first guide face is composed of only the face parallel to the second straight line, and thus the first guide face can reliably guide the fluid guided to the first fluid route to the surface of the observation window.

In the present invention, a fluid injected from the fluid injection nozzle can reliably flow to the observation window and the region adjacent to the observation window and cleaning performance or wiping performance for the observation window can be improved.

DETAILED DESCRIPTION OF THE EMBODIMENTS

Hereinafter, referring to accompanying drawings, preferable embodiments of the present invention will be described in detail.

Figure 1:
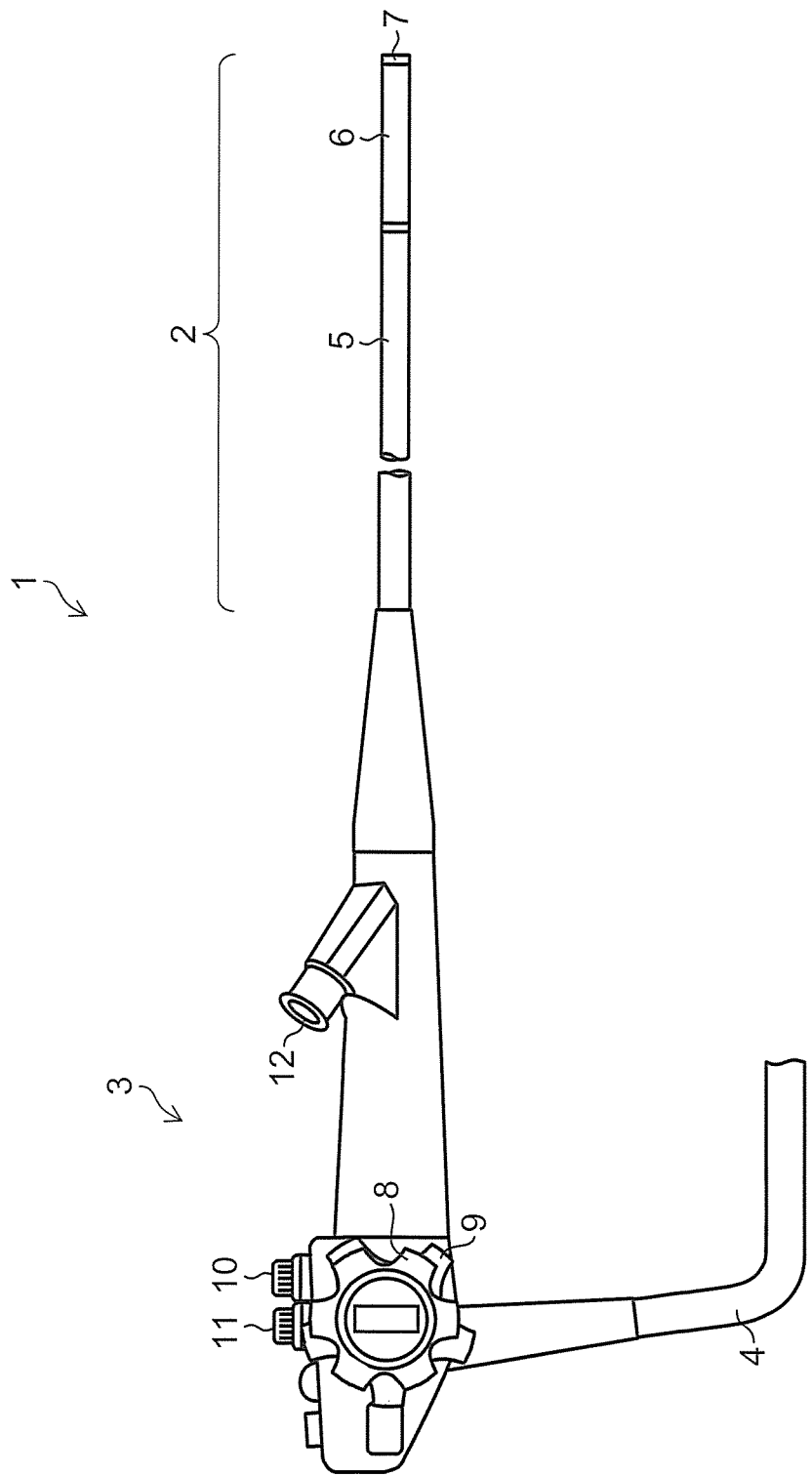
FIG. 1 is a general view of an endoscope to which the present invention is applied.

FIG. 1 is a configuration diagram showing an endoscope 1 in accordance with the present invention.

The endoscope 1 in FIG. 1 includes: an insertion section 2 that is to be inserted into a patient's body; an operation section 3 that is connected to a proximal end of the insertion section 2 to be used for holding the endoscope 1, operating the insertion section 2, and the like; and an universal code 4 that connects the endoscope 1 to system configuration devices, such as a light source device (not shown) and a processor device.

The insertion section 2 has a distal end, a proximal end, and a longitudinal axis. The insertion section 2 includes a flexible part 5, a bending part 6, and a distal end part 7, which are connected in this order from the proximal end toward the distal end. The flexible part 5 has flexibility to curve in any direction along an insertion path of the insertion section 2. The bending part 6 is bendable in each of directions of up and down, and right and left, by operating angle knobs 8 and 9 of the operation section 3. The distal end part 7 includes an observation part that takes an image of an observation target site in a body, an illumination part that irradiates the observation target site with an illumination light.

Figure 2:
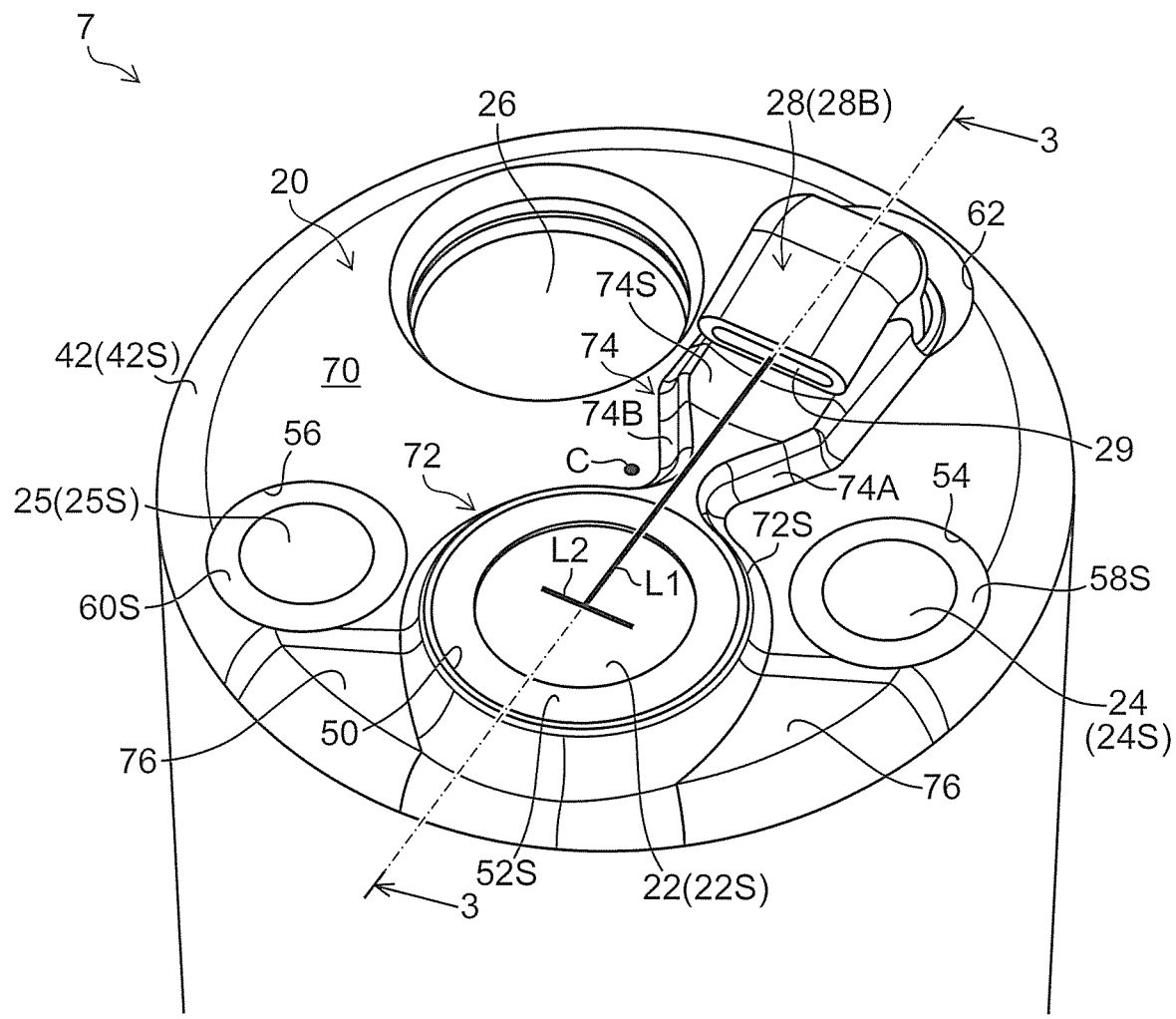
FIG. 2 is a perspective view of a distal end part of the endoscope, and shows structure of a distal end face of a first embodiment.

FIG. 2 is a perspective view showing the distal end part 7 in an enlarged manner.

As shown in FIG. 2, the distal end part 7 is provided with a distal end face 20 along a plane substantially perpendicular to the longitudinal axis that is an axis of the insertion section 2. The distal end face 20 includes an observation window 22, illumination windows 24 and 25, a treatment tool exit port 26, a fluid injection nozzle 28, and the like. Hereinafter, when a term of "longitudinal axis" is simply used, it indicates the longitudinal axis of the insertion section 2.

The observation window 22 is a component of the observation part that captures an image of the observation target site. Through the observation window 22, a subject light from the observation target site is acquired by other components of the observation part such as an optical system (such as an imaging lens) and an imaging device. An image taken by the observation part is transmitted to a processor device connected with the universal code 4, as an observation image (endoscope image).

The illumination windows 24 and 25 are components of the illumination part mounted in the distal end part 7. Through the illumination windows 24 and 25, the observation target site is irradiated with an illumination light emitted from a light emission part that is another component of the illumination part. The illumination light emitted from the light emission part is propagated from the light source device connected with the universal code 4 through a light guide inserted inside the endoscope 1.

The treatment tool exit port 26 communicates with a treatment tool entry port 12 of the operation section 3 (refer to FIG. 1) through a treatment tool insertion channel passing through inside the insertion section 2. Through the treatment tool exit port 26, a treatment tool inserted from the treatment tool entry port 12 is guided out.

The treatment tool insertion channel is coupled to a suction channel, and a suction button 11 of the operation section 3 (refer to FIG. 1) is operated to perform suction through the treatment tool exit port 26.

The fluid injection nozzle 28 is provided with an injection port 29 that is an aperture for injecting fluid, and that faces the observation window 22 to inject cleaning liquid or gas to a surface 22S of observation window 22 and the periphery of the surface 22S.

The fluid injection nozzle 28 communicates with an air-supply/water-supply channel passing through the inside of the endoscope 1, and is connected to an air-supply/water-supply device (not shown), to which the universal code 4 is connected, through the air-supply/water-supply channel.

When a leak hole formed in an air-supply/water-supply button 10 of the operation section 3 (refer to FIG. 1) is closed by a finger, the fluid injection nozzle 28 injects gas from the air-supply/water-supply device. When the air-supply/water-supply button 10 is depressed by the finger closing the leak hole, the fluid injection nozzle 28 injects cleaning liquid from the air-supply/water-supply device.

A procedure of cleaning the observation window 22 is, for example, as follows: the fluid injection nozzle 28 injects cleaning liquid to remove accretions, such as blood and body fluid, adhering to the observation window 22; and then, the fluid injection nozzle 28 injects gas to remove the cleaning liquid remaining on the observation window 22 or a region adjacent thereto.

Next, the structure of the distal end face 20, particularly the structure related to a flow channel of fluid injected from the fluid injection nozzle 28, will be described in detail.

Figure 3:
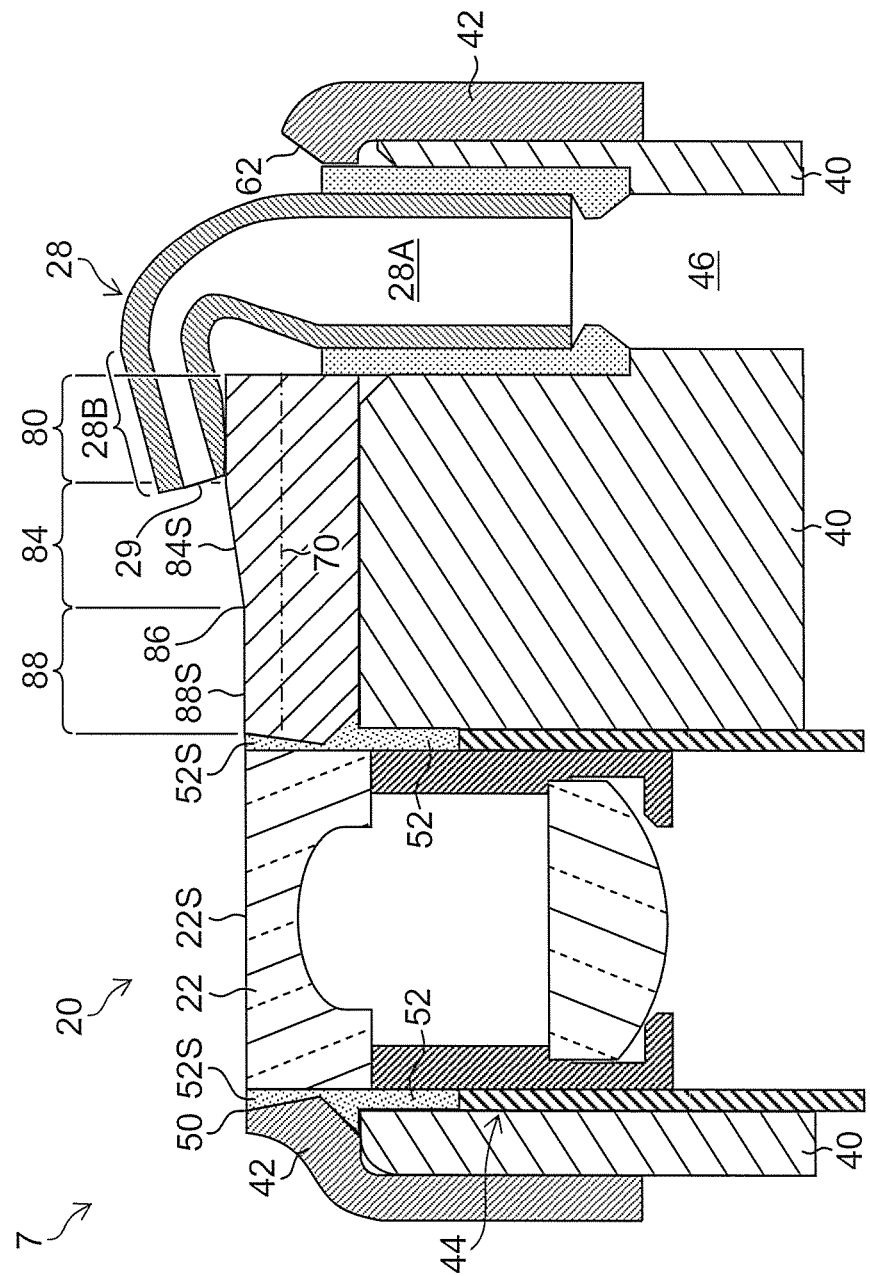
FIG. 3 is a sectional view of the distal end as viewed from a direction of arrows 3-3 in FIG. 2.

The perspective view of the distal end 7 shown in FIG. 2 shows the structure of a first embodiment of the distal end face 20. FIG. 3 is a sectional view of the distal end part 7 as viewed from a direction of the arrow of the 3-3 line in FIG. 2.

As shown in FIG. 3, the distal end part 7 is formed of hard materials, such as a metal, and includes a distal end body 40 that holds various components arranged in the distal end part 7, and a distal end cover 42 which is formed of an insulation resin material and covers a distal end and a side surface (peripheral surface) of the distal end body 40.

FIG. 3 shows, as components held in the distal end body 40, a lens barrel 44 that constitutes the observation part and accommodates the imaging lens and the observation window 22, and an edge of an air-supply/water-supply channel 46 connected to the fluid injection nozzle 28. In the present embodiment, an optical axis of the observation window 22 (and the imaging lens) is substantially parallel the longitudinal axis of the insertion section 2.

As shown in FIG. 2, the distal end face 20 of the distal end part 7 is mainly formed to have a circular flat surface that is perpendicular to the longitudinal axis of the insertion section 2, and that intersects with the longitudinal axis at a center "C" (hereinafter, referred to as the center "C" of the distal end face 20).

The distal end face 20 is provided with a surface 42S on a distal end side of the distal end cover 42, a surface 22S of the observation window 22, surfaces 24S and 25S of the illumination windows 24 and 25, the treatment tool exit port 26 that is an opening formed in the distal end cover 42, and the fluid injection nozzle 28.

The surface 22S of the observation window 22, for example, is composed of a flat surface, and is arranged perpendicular to the longitudinal axis of the insertion section 2, that is, the optical axis of the observation window 22, as well as arranged in an opening 50 formed in the distal end cover 42. The center of the circular surface 22S is arranged at a position displaced toward the circumference of the distal end face 20 with respect to the center "C" of the distal end face 20.

A space communicating with the inside of the distal end part 7 from a gap between the circumference of the surface 22S of the observation window 22 and the circumference of the opening 50 is filled with an adhesive 52 (refer to FIG. 3). A surface 52S of the adhesive 52 is arranged between the circumference of the surface 22S of the observation window 22 and the circumference of the opening 50 to be flush with the surface 22S.

Each of the surfaces 24S and 25S of the illumination windows 24 and 25 is formed into a flat surface, for example, and is arranged perpendicular to the longitudinal axis of the insertion section 2. The surfaces 24S and 25S are arranged in openings 54 and 56 formed in the distal end cover 42, respectively. The centers of the circular surfaces 24S and 25S are respectively arranged at positions which are displaced toward the circumference of the distal end face 20 with respect to the center "C" of the distal end face 20, and are substantially opposite to each other across the center of the surface 22S of the observation window 22.

As with the above-mentioned surface 52S of the adhesive 52 between the circumference of the surface 22S of the observation window 22 and the circumference of the opening 50, surfaces 58S and 60S of adhesive are arranged between the circumference of the surface 24S and the circumference of the opening 54, and between the circumference of the surface 25S and the circumference of the opening 56, respectively, and the surfaces 58S and 60S are arranged flush with the surfaces 24S and 25S, respectively.

The fluid injection nozzle 28, as shown in FIG. 3, is formed in an L-shape from a proximal end part 28A connected to the edge of the air-supply/water-supply channel 46 to a distal end part 28B provided with the injection port 29. The distal end part 28B of the fluid injection nozzle 28 is arranged to project to a distal end side of the insertion section 2 in a longitudinal axial direction through an opening 62 formed in the distal end cover 42.

The injection port 29 of the fluid injection nozzle 28 is arranged to face toward the direction of the observation window 22. That is, the injection port 29 is a rectangular opening (a plane) that is substantially perpendicular to an axis of a conduit line of the fluid injection nozzle 28. When the distal end face 20 is viewed from the front in the longitudinal axial direction, the injection port 29 is arranged so that a normal line passing through the center of the injection port 29 faces toward an approximate center of the surface 22S of the observation window 22.

The proximal end part 28A of the fluid injection nozzle 28 has a conduit line whose cross-section perpendicular to an axis of the conduit line has a circular shape. The center of the conduit line is arranged at a position which is displaced toward the circumference of the distal end face 20 with respect to the center "C" of the distal end face 20 and is closer to the illumination window 24 than the illumination window 25 to avoid interference with the treatment tool exit port 26.

Between an outer wall surface of the fluid injection nozzle 28 and the circumference of the opening 62, a surface of an adhesive (not shown) is arranged.

The surface 42S of the distal end cover 42 includes a flat reference plane 70 that occupies almost entire region of the surface 42S and is perpendicular to the longitudinal axis of the insertion section 2, and a stepped part 72 and a guide part 74 which project toward the distal end side from the reference plane 70. The stepped part 72 and the guide part 74 relate to control of a flow channel of fluid injected from the fluid injection nozzle 28 as described below. The control of the flow channel of the fluid improves wiping performance of removing cleaning liquid and the like when the observation window 22 is cleaned.

The stepped part 72 is formed throughout the circumference of the opening 50 in which the surface 22S of the observation window 22 is arranged, and includes a stepped face 72S that is formed by raising the whole of the circumference of the opening 50 toward the distal end side from the reference plane 70. With formation of the stepped part 72, the surface 22S of the observation window 22 and the surface 52S of the adhesive 52 are arranged at a position projecting toward the distal end side by a height of the stepped part 72 (the amount of projection with respect to the reference plane 70) with respect to the reference plane 70.

From the circumference of the opening 62 in which the fluid injection nozzle 28 is arranged to the stepped part 72 (the circumference of the opening 50), the guide part 74 is formed so as to be projected from the reference plane 70 toward the distal end side at a position along a straight line connecting the center of the opening 62 and the center of the opening 50.

When a straight line connecting between the center of the fluid injection nozzle 28 (the center of the injection port 29) and the center of the surface 22S of the observation window 22 is indicated as a first straight line L1, the guide part 74 includes a guide face 74S that is composed of only a face parallel to a second straight line L2 orthogonal to the first straight line L1 and the longitudinal axis, and side faces 74A and 74B that connect the guide face 74S projecting toward the distal end side with respect to the reference plane 70 with the reference plane 70 on both sides of the guide face 74S.

In the surface 42S of the distal end cover 42 on an observation window 22 side opposite to the fluid injection nozzle 28, there is provided a liquid discharge part 76 that is recessed toward a proximal end side in the longitudinal axial direction from the reference plane 70. When the fluid injection nozzle 28 injects a gas after injecting cleaning liquid, and even if the cleaning liquid remains in a region on the observation window 22 side opposite to the fluid injection nozzle 28, the region where a flow channel of the gas is hardly made, the liquid discharge part 76 as the region recessed toward the proximal end side from the reference plane 70 prevents the cleaning liquid remaining in the liquid discharge part 76 from affecting an observation image.

Subsequently, structure and operation of the stepped part 72 and the guide part 74 of the distal end face 20 will be described with reference to a relationship with a flow channel of fluid injected from the fluid injection nozzle 28.

Hereinafter, terms of "distal end side" and "proximal end side" represent respectively a distal end side and a proximal end side in the longitudinal axial direction of the insertion section 2.

Figure 4:
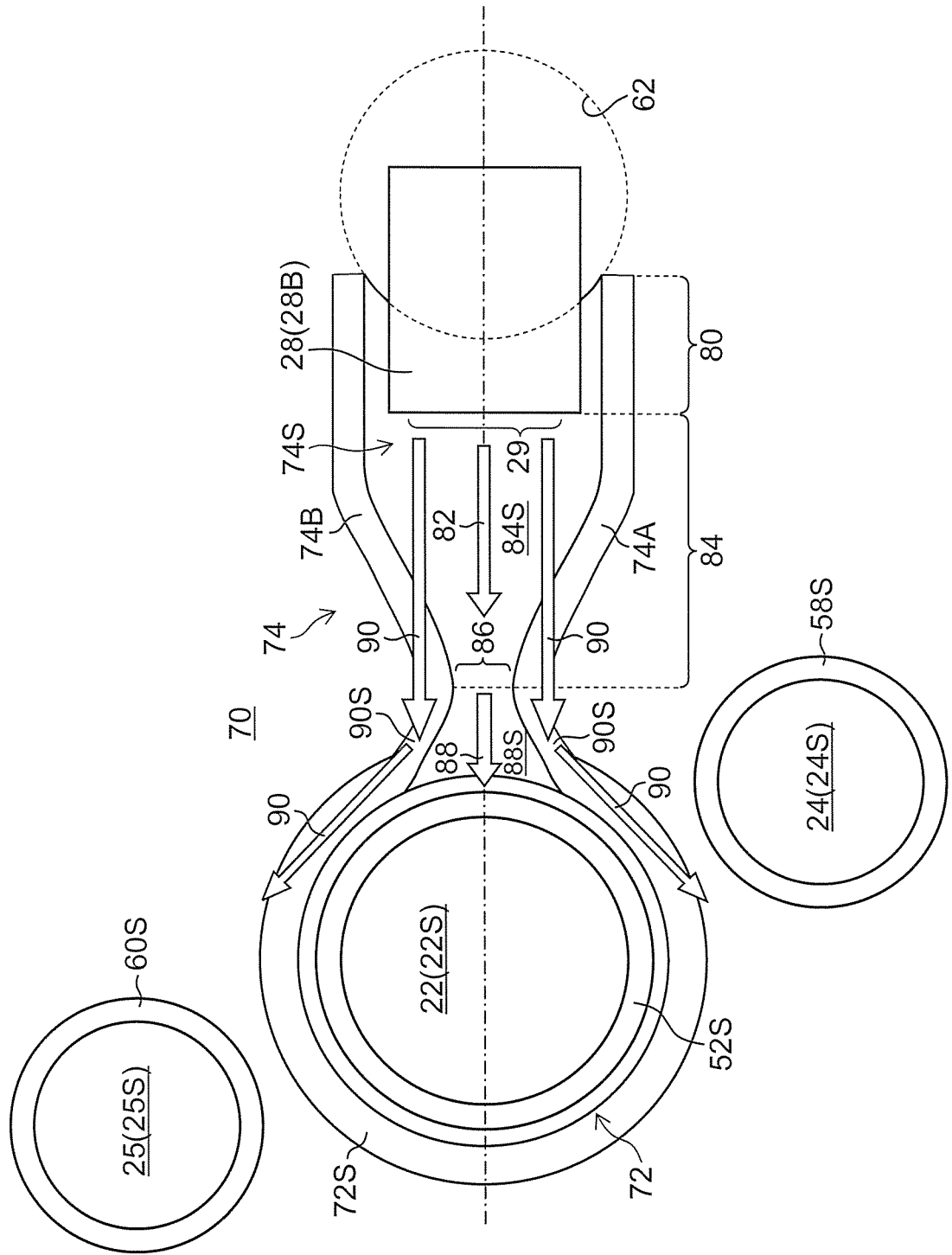
FIG. 4 is a plan view of the distal end face as viewed from the front in a longitudinal axial direction, and is a schematic view that briefly shows a region between a fluid injection nozzle and a surface of an observation window, and the periphery of the region.

FIG. 4 is a plan view of the distal end face 20 as viewed from the front in the longitudinal axial direction, and is a schematic view that briefly shows a region between the fluid injection nozzle 28 and the surface 22S of the observation window 22, and the periphery of the region.

As shown in FIG. 4, the distal end face 20 includes: a nozzle support part 80 that positions the distal end part 28B (injection port 29) of the fluid injection nozzle 28 on the distal end side from the reference plane 70 in accordance with the stepped part 72 and the guide part 74, described above; a proximal end route 82 through which fluid is guided from the injection port 29 of the fluid injection nozzle 28 to a fluid guiding part 86 described below; a fluid initial passing part 84 that forms a part (proximal end part) of a second fluid route 90 described below from the injection port 29 of the fluid injection nozzle 28; the fluid guiding part 86 that is provided at a position between the fluid injection nozzle 28 and the observation window 22 to guide a part of fluid injected from the fluid injection nozzle 28 to an observation window 22 side; a first fluid route 88 through which the part of fluid guided by the fluid guiding part 86 is guided to the observation window 22; and a second fluid route 90 through which the fluid deviated from the fluid guiding part 86 in the fluid injected from the fluid injection nozzle 28 is at least guided to a region adjacent to the observation window 22 (surface 22S).

The nozzle support part 80 shows a range of the guide face 74S of the guide part 74 that is a proximal end side (a proximal end side in the longitudinal axial direction) of the distal end part 28B of the fluid injection nozzle 28, or a range of the guide face 74S from the circumference of the opening 62 of the distal end cover 42 to the injection port 29 of the fluid injection nozzle 28.

As shown in FIG. 3, the nozzle support part 80 is formed as a plane perpendicular to the longitudinal axis, on the distal end side from the reference plane 70, and abuts on the distal end part 28B of the fluid injection nozzle 28 so as to support the distal end part 28B of the fluid injection nozzle 28 at a position on the distal end side from the reference plane 70.

Accordingly, as compared with the case where the distal end part 28B of the fluid injection nozzle 28 is supported by the reference plane 70, the injection port 29 is arranged further toward the distal end side within a range where the fluid injection nozzle 28 does not come into observation visual field. As the injection port 29 is arranged further toward the distal end side, an injecting direction of fluid injected from the injection port 29 approaches a direction perpendicular to the surface 22S of the observation window 22 (the longitudinal axial direction). As a result, the flow velocity of fluid is increased to improve cleaning performance or wiping performance of removing cleaning liquid.

The fluid initial passing part 84 includes a third guide face 84S that is continuously connected to the nozzle support part 80 to guide fluid immediately after injected from the fluid injection nozzle 28. A range from the injection port 29 of the fluid injection nozzle 28 to the fluid guiding part 86 described later in the guide face 74S of the guide part 74 is used as the third guide face 84S.

As shown in FIG. 3, the third guide face 84S is a plane that is arranged on the distal end side from the reference plane 70, obliquely intersects with the longitudinal axis, and is formed as a third inclined surface that inclines toward the proximal end side as a distance from the injection port 29 increases.

As shown in FIG. 4, when the distal end face 20 is viewed from the front in the longitudinal axial direction, the third guide face 84S is formed so as to gradually decrease in width (width in a direction of the second straight line L2 described above) toward the first straight line L1 described above connecting between the center of the fluid injection nozzle 28 (the center of the injection port 29) and the center of the surface 22S of the observation window 22, from the injection port 29 toward the fluid guiding part 86.

Accordingly, some fluid injected from near a center part of the injection port 29 in fluid injected from the injection port 29 is guided to the fluid guiding part 86 through the proximal end route 82 in the fluid initial passing part 84.

Fluid (a part of fluid) deviated from the proximal end route 82 of the fluid initial passing part 84 in the fluid injected from the injection port 29 is guided from the third guide face 84S in a direction of the side faces 74A and 74B of the guide part 74. In this way, a part of the third guide face 84S, through which the fluid guided to the direction of the side faces 74A and 74B passes, forms a part of the second fluid route 90 described later.

The fluid guiding part 86 is continuously connected to the fluid initial passing part 84, and represents a proximal end part of the first fluid route 88 described later through which fluid is guided to the surface 22S of the observation window 22, or represents a position closest to the injection port 29, within a range of the guide face 74S, through which fluid is guided only to the surface 22S of the observation window 22.

In the present embodiment, the guide face 74S has narrowed width (width in the direction of the second straight line L2), and a part (position) with the narrowest width of the guide face 74S corresponds to the fluid guiding part 86.

Width of the fluid guiding part 86 in the direction of the second straight line L2 is less than opening width of the injection port 29 of the fluid injection nozzle 28 in the direction of the second straight line L2.

Accordingly, a part of fluid injected from the injection port 29 can be guided to the second fluid route 90, and the width of the fluid guiding part 86 can be adjusted so that fluid flows to the second fluid route 90 at an appropriate flow rate.

It is desirable that the width of the fluid guiding part 86 is one-fourth or more of the opening width of the injection port 29, for example, to prevent a flow rate of fluid guided to the observation window 22 from being too small.

The first fluid route 88 includes a first guide face 88S that is continuously connected to the fluid guiding part 86 to guide fluid guided at the fluid guiding part 86 to the surface 22S of the observation window 22. A range from the fluid guiding part 86 to the surface 22S of the observation window 22 (the surface 52S of the adhesive 52) of the guide face 74S of the guide part 74 is used as the first guide face 88S.

As shown in FIG. 3, the first guide face 88S is formed as a plane perpendicular to the longitudinal axis on the distal end side from the reference plane 70, and is formed at a position to be flush with the surface 22S of the observation window 22 and the surface 52S of the adhesive 52.

That is, the first guide face 88S is composed of a continuous face connecting between the fluid guiding part 86 and the surface 22S of the observation window 22, and has no step.

In the present specification, "step" or "stepped face" means the one which changes a flowing direction of fluid injected from the fluid injection nozzle 28 to a direction orthogonal to the longitudinal axis (the optical axis of the observation window 22), and thus the "step" or the "stepped face" does not include a component which changes the flowing direction only in the longitudinal axial direction, such as an inclined surface that gradually inclines to the distal end side in the longitudinal axial direction or the proximal end side as a distance from the fluid injection nozzle 28 increases.

As shown in FIG. 4, when the distal end face 20 is viewed from the front in the longitudinal axial direction, the first guide face 88S is formed so as to gradually increase in width in the direction of the second straight line L2 described above from the fluid guiding part 86 to a position of the surface 52S of the adhesive 52 from the first straight line L1 described above as the center.

Accordingly, fluid guided to the first fluid route 88 after passing through the fluid guiding part 86 is guided to the surface 22S of the observation window 22 while causing little curvature in a direction other than the longitudinal axial direction (direction perpendicular to the longitudinal axis), at least.

Thus, fluid guided to the first fluid route 88 at the fluid guiding part 86 through the proximal end route 82 of the fluid initial passing part 84 after injected from the injection port 29 is reliably guided to the surface 22S of the observation window 22 at least through the first fluid route 88.

Here, fluid directly guided to the first fluid route 88, even if the fluid is deviated from the fluid guiding part 86, is guided to the surface 22S of the observation window 22 through the first fluid route 88.

The second fluid route 90 includes a second guide face 90S that guides a part of fluid injected from the fluid injection nozzle 28, that is, fluid deviated from the fluid guiding part 86, to at least a region adjacent to the observation window 22 (surface 22S), the. The second fluid route 90 has, as the second guide face 90S, at least one range of a range of the stepped face 72S of the stepped part 72 (e.g., a portion of the stepped face 72S that is adjacent to the fluid guiding part 86) and a range of the side faces 74A and 74B of the guide part 74 (e.g., a portion of each of the side faces 74A and 74B that is located besides the first guide face 84S).

As described above, the second fluid route 90 includes a guide face that guides fluid (some fluid) deviated from the proximal end route 82 of the fluid initial passing part 84 in fluid injected from the injection port 29 to the second guide face 90S, and as described above, a part of a range of the third guide face 84S is included as the guide face.

The second fluid route 90 serves as a route allowing fluid to be guided to not only a region adjacent to the observation window 22, but also a peripheral region of the observation window 22, including a peripheral region within a range of the observation window 22 (surface 22S), by bending a flow channel of fluid in a direction orthogonal to the longitudinal axis.

An observation window 22 side of the second guide face 90S projects toward the distal end side more than a fluid injection nozzle 28 side thereof, and the second guide face 90S represents a face (stepped face) including a step having a component obliquely intersecting with the first straight line L1 described above when the distal end face 20 is viewed from the front in the longitudinal axial direction as shown in FIG. 4.

Accordingly, the second guide face 90S bends fluid guided to the second guide face 90S after injected from the injection port 29 in a direction perpendicular to the longitudinal axis with respect to a flowing direction like the second fluid route 90 of FIG. 4, that is, in a direction separated from the first straight line L1 when the distal end face 20 is viewed from the front in the longitudinal axial direction. Thus, the fluid passing through the second fluid route 90 is guided to the peripheral region of the observation window 22.

It is desirable that the stepped face constituting the second guide face 90S includes at least a face parallel to the longitudinal axis (the optical axis of the observation window 22).

The structure of the stepped part 72 and the guide part 74 in the distal end face 20 of the first embodiment described above allows fluid guided through the second fluid route 90 to be sprayed to the periphery region of the observation window 22 as intended. Thus, it is possible to clean throughout the whole of the surface 22S of the observation window 22 and the periphery of the surface 22S with cleaning liquid.

When the fluid injection nozzle 28 injects gas after injecting cleaning liquid, the gas guided through the second fluid route 90 reliably and immediately blows away the cleaning liquid existing in the periphery region of the surface 22S of the observation window 22 and the cleaning liquid blown away to the periphery region from near the center of the surface 22S.

Particularly, in the case where the illumination windows 24 and 25 exist near the observation window 22 like the present embodiment, cleaning liquid tends to easily remain in a space between the observation window 22 and the illumination windows 24 and 25, however, even such cleaning liquid is reliably and immediately removed.

Thus, not only deterioration of an observation image caused by cleaning liquid remaining on the surface 22S of the observation window 22, but also deterioration of an observation image, such as halation or limb darkening caused by the cleaning liquid remaining in the periphery region of the observation window 22, is reliably and easily prevented.

The embodiment described above shows the guide face 74S of the guide part 74 in which: the first guide face 88S of the first fluid route 88 that is formed by the guide face 74S of the guide part 74 between the injection port 29 of the fluid injection nozzle 28 and the surface 22S of the observation window 22 as shown in FIG. 3, is formed as a plane perpendicular to the longitudinal axial direction; and the third guide face 84S of the fluid initial passing part 84 is formed as the third inclined surface which is inclined to the distal end side as a distance from the fluid injection nozzle 28 increases.

Each of FIGS. 5A to 5E is a simplified diagram that shows a position relation in the longitudinal axial direction among the injection port 29 of the fluid injection nozzle 28, the third guide face 84S, the fluid guiding part 86, the first guide face 88S, the surface 52S of the adhesive 52, and the surface 22S of the observation window 22, showing a plurality of forms.

Although the embodiment described above employs the form of FIG. 5A, any one of forms shown in each of FIGS. 5B to 5E may be employed.

Figure 5A:
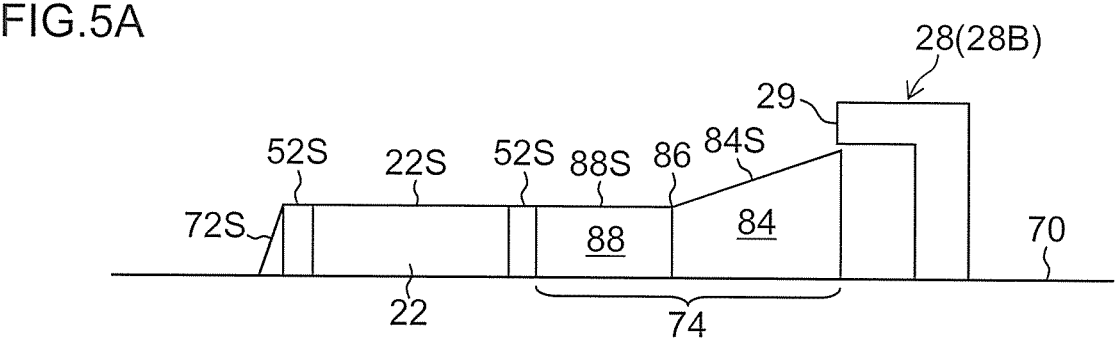
FIGS. 5A to 5E are simplified diagrams illustrating examples of a position relation in the longitudinal axial direction among an injection port of the fluid injection nozzle, a third guide face, a fluid guiding part, a first guide face, a surface of an adhesive, and the surface of the observation window.
Figure 5B:
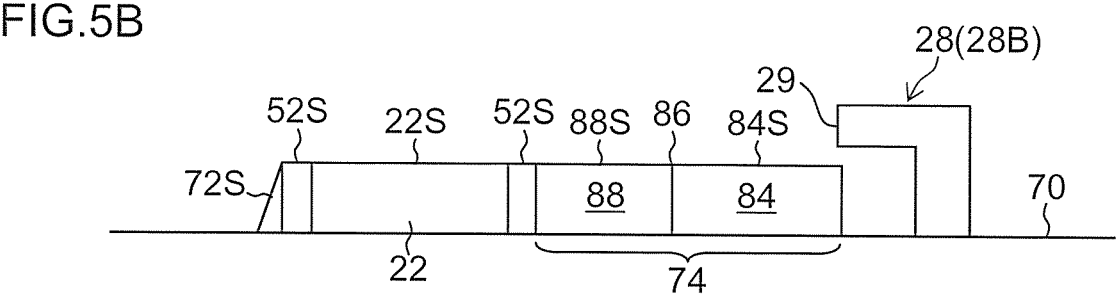

In FIG. 5B, on the distal end side from the reference plane 70, both of the first guide face 88S and the third guide face 84S are formed at a position to be flush with the surface 22S of the observation window 22 and the surface 52S of the adhesive 52, as a plane perpendicular to the longitudinal axis.

Figure 5C:
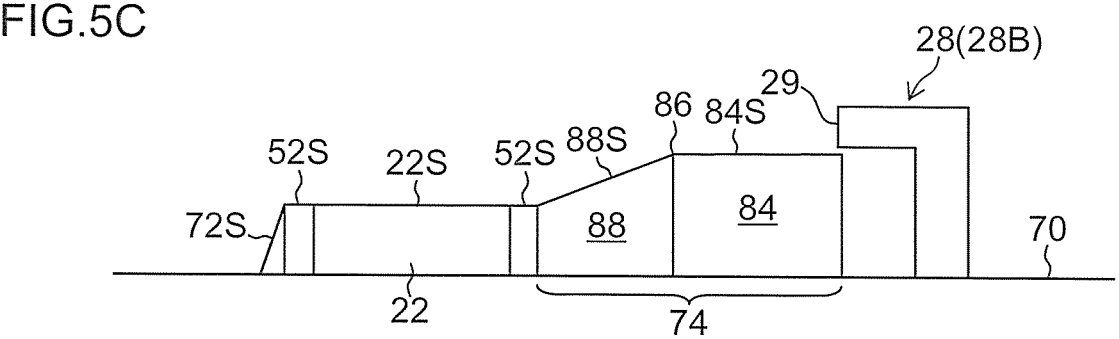

In FIG. 5C, on the distal end side from the reference plane 70, the first guide face 88S is formed to be continuously connected to the surface 22S of the observation window 22 and the surface 52S of the adhesive 52, as a second inclined surface inclined to the proximal end side from the fluid guiding part 86 to the observation window 22, and the third guide face 84S is formed to be continuously connected to the first guide face 88S, as a plane perpendicular to the longitudinal axis.

Figure 5D:
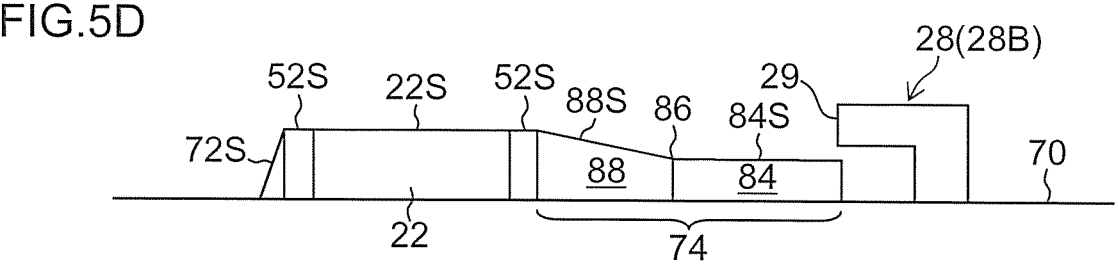

In FIG. 5D, on the distal end side from the reference plane 70, the first guide face 88S is formed to be continuously connected to the surface 22S of the observation window 22 and the surface 52S of the adhesive 52, as a first inclined surface inclined to the distal end side from the fluid guiding part 86 to the observation window 22, and the third guide face 84S is formed to be continuously connected to the first guide face 88S, as a plane perpendicular to the longitudinal axis.

Figure 5E:
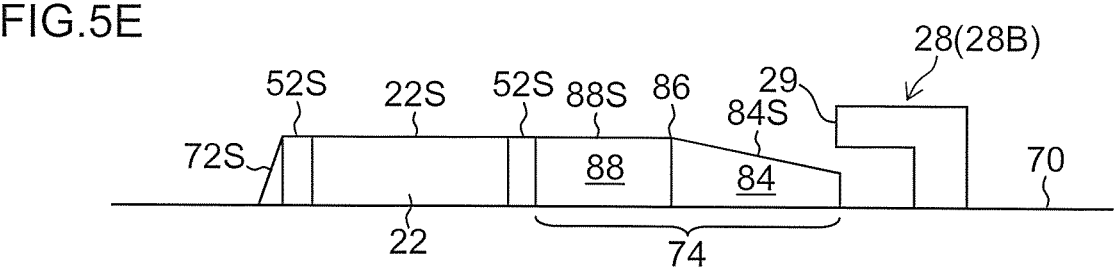

In FIG. 5E, on the distal end side from the reference plane 70, the first guide face 88S is formed to be continuously connected to the surface 22S of the observation window 22 and the surface 52S of the adhesive 52, and as well as formed to be flush therewith, as a plane perpendicular to the longitudinal axis, and the third guide face 84S is formed to be continuously connected to the first guide face 88S as an inclined surface that inclines to the distal end side as a distance from the fluid injection nozzle 28 increases.

In the distal end face 20 of the embodiment described above, a fluid holding region may be provided in a region adjacent to the observation window 22 to hold liquid.

Accordingly, when the fluid injection nozzle 28 injects gas, cleaning liquid existing on the surface 22S of the observation window 22 can be easily guided to the fluid holding region, and thus the gas guided through the second fluid route 90 can reliably remove the cleaning liquid held in the fluid holding region.

The following forms are available as specific forms constituting the fluid holding region: a form in which a surface energy of a solid surface in a region to be the fluid holding region is set higher than that in the periphery of the region (at least on an observation window 22 side) so as to allow cleaning liquid to easily adhere; and a form in which a recessed part is formed in a region to be the fluid holding region so as to allow cleaning liquid to be easily stored.

Here, a high surface energy of a solid surface indicates that liquid can easily adhere to the solid surface, and corresponds to a large wettability or a small water repellency. Then, any means to make the surface energy higher than that of the periphery by the following is available: difference in material from the periphery; chemical surface treatment; and fine convexo-concave structure. For example, a form in which the distal end cover 42 is made of a material with a surface energy higher than that of each of the surface 22S of the observation window 22 and the surface 52S of the adhesive 52 may be adopted. Although the form adopting the fine convexo-concave structure corresponds also to a form in which a recessed part is formed in a region to be the fluid holding region, the form includes a form in which fine convexo-concaves (asperities) are formed on a surface by emboss processing, hairline processing, or the like, even if a concave part cannot be observed as a recessed part in appearance.

Forming a recessed part in a region to be the fluid holding region includes not only the case where the whole of the region is recessed with respect to the periphery, but also the case where a plurality of asperities (two or more recessed parts, or a large number of convexo-concaves) is formed.

The fluid holding region may be provided not only in the whole of the circumference of the surface 22S of the observation window 22, but also partially in the circumference of the surface 22S of the observation window 22.

For example, in the embodiment described above, it is preferable that the fluid holding region is provided in a limited region including a region between the observation window 22, and the illumination windows 24 and 25, because fluid guided through the second fluid route 90 tends to be easily guided to the region between the observation window 22, and the illumination windows 24 and 25. Thus, gas guided through the second fluid route 90 can reliably and immediately blow away the cleaning liquid held in the fluid holding region to a region where the cleaning liquid does not affect an observation image, such as the liquid discharge part 76.

In the embodiment described above, arrangement (position relation) of the observation window 22, the illumination windows 24 and 25, the treatment tool exit port 26, the fluid injection nozzle 28, and the like, in the distal end face 20, is an example, and thus the arrangement of those components is not limited to specific arrangement.

Next, a distal end face of another embodiment having the same effect of a flow channel of fluid injected from the fluid injection nozzle 28, as that of the distal end face 20 of the first embodiment described above, will be described.

In the description below, a component with the same or similar operation as that of the component of the distal end face 20 of the first embodiment is designated by the same reference numeral used in the first embodiment to omit duplicated description.

Moreover, regarding the distal end face of the other embodiment below, the structure of the stepped part 72 and the guide part 74 related to a flow channel of the fluid injected from the fluid injection nozzle 28 will be mainly described as differences from the first embodiment. Forms of other components are shown, for example, and thus a different form can be appropriately used.

A preferable shape of each of the stepped part 72 and the guide part 74 in the distal end face of the distal end part 7 of the endoscope 1 varies depending on the following elements 1 to 5:

1. Position of the fluid injection nozzle 28 in the longitudinal axial direction (direction of the optical axis of the observation window 22);
2. Distance between the fluid injection nozzle 28 and the observation window 22;
3. Relationship between opening width of the fluid injection nozzle 28 (opening width in a direction of the second straight line L2 described above) and a diameter of the observation window 22;
4. Distance between the observation window 22, and the illumination windows 24 and 25; and
5. Injecting force from the fluid injection nozzle 28.

Thus, a specific form of each of the stepped part 72 and the guide part 74 is not limited to the form of the distal end face 20 of the first embodiment described above, and thus forms shown in FIGS. 6 to 10 can be adopted, for example, depending on the elements 1 to 5, or the like.

Figure 6:
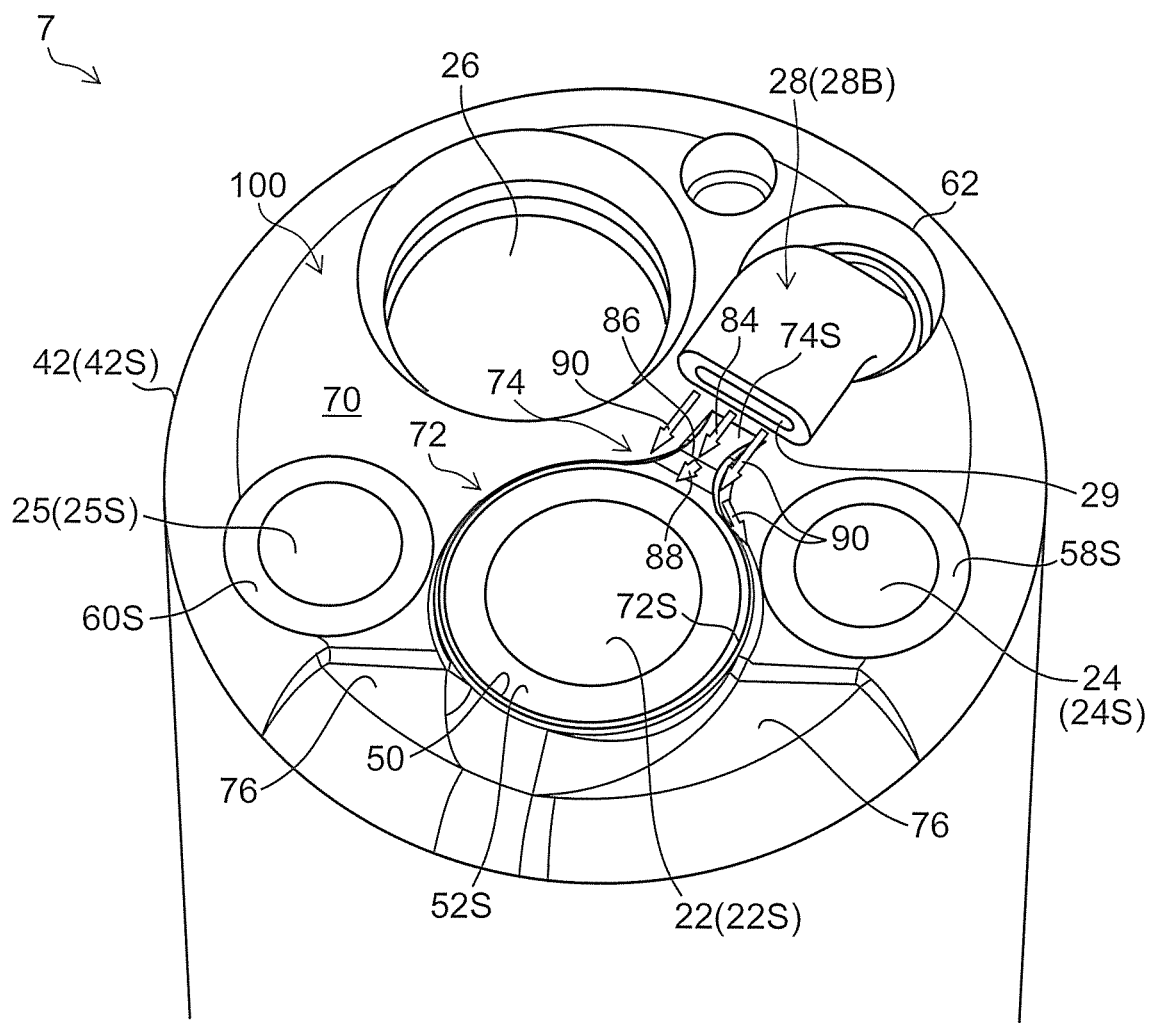
FIG. 6 is a perspective view of a distal end part including a distal end face of a second embodiment.

FIG. 6 is a perspective view of the distal end part 7 including a distal end face 100 of a second embodiment.

The distal end face 100 in FIG. 6 does not include the nozzle support part 80 as the stepped part 72 and the guide part 74, among the nozzle support part 80, the fluid initial passing part 84, the fluid guiding part 86, the first fluid route 88, and the second fluid route 90, in the distal end face 20 of the first embodiment. In addition, the distal end face 100 has the fluid initial passing part 84 which is greatly different from that in the distal end face 20.

That is, the guide part 74 is formed from a position separated from the injection port 29 of the fluid injection nozzle 28, and the guide face 74S of the guide part 74 is an inclined surface that inclines to the distal end side in the longitudinal axial direction as a distance to the observation window 22 decreases. A width of the guide face 74S is provided with a narrowed part (constriction).

Thus, the guide part 74 does not include the nozzle support part 80, and the distal end part 28B of the fluid injection nozzle 28 is arranged at a position where the distal end part 28B directly abuts on the reference plane 70 of the distal end cover 42. For example, in the case where the distance between the fluid injection nozzle 28 and the observation window 22, described above, is reduced, a form without the nozzle support part 8, such as the guide part 74 of the present embodiments (and the third to sixth embodiments that are shown in FIGS. 7 to 10), may be adopted in order to prevent the fluid injection nozzle 28 from coming into the observation visual field, and so on.

A guide face of the fluid initial passing part 84 is composed of the guide face 74S of the guide part 74 from a position separated from the reference plane 70 perpendicular to the longitudinal axis and the injection port 29, the guide face 74S inclining to the distal end side in the longitudinal axial direction as a distance from the fluid injection nozzle 28 increases.

Here, a part of the guide face 74S where the width is the narrowest, serves as the fluid guiding part 86, and the width in the fluid guiding part 86 is less than the opening width of the injection port 29 of the fluid injection nozzle 28, as with the first embodiment.

A range from the fluid guiding part 86 to the guide face 74S of the guide part 74 on an observation window 22 side constitutes a guide face (first inclined surface) of the first fluid route 88, which inclines to the distal end side in the longitudinal axial direction from the fluid guiding part 86 toward the observation window 22.

Figure 7:
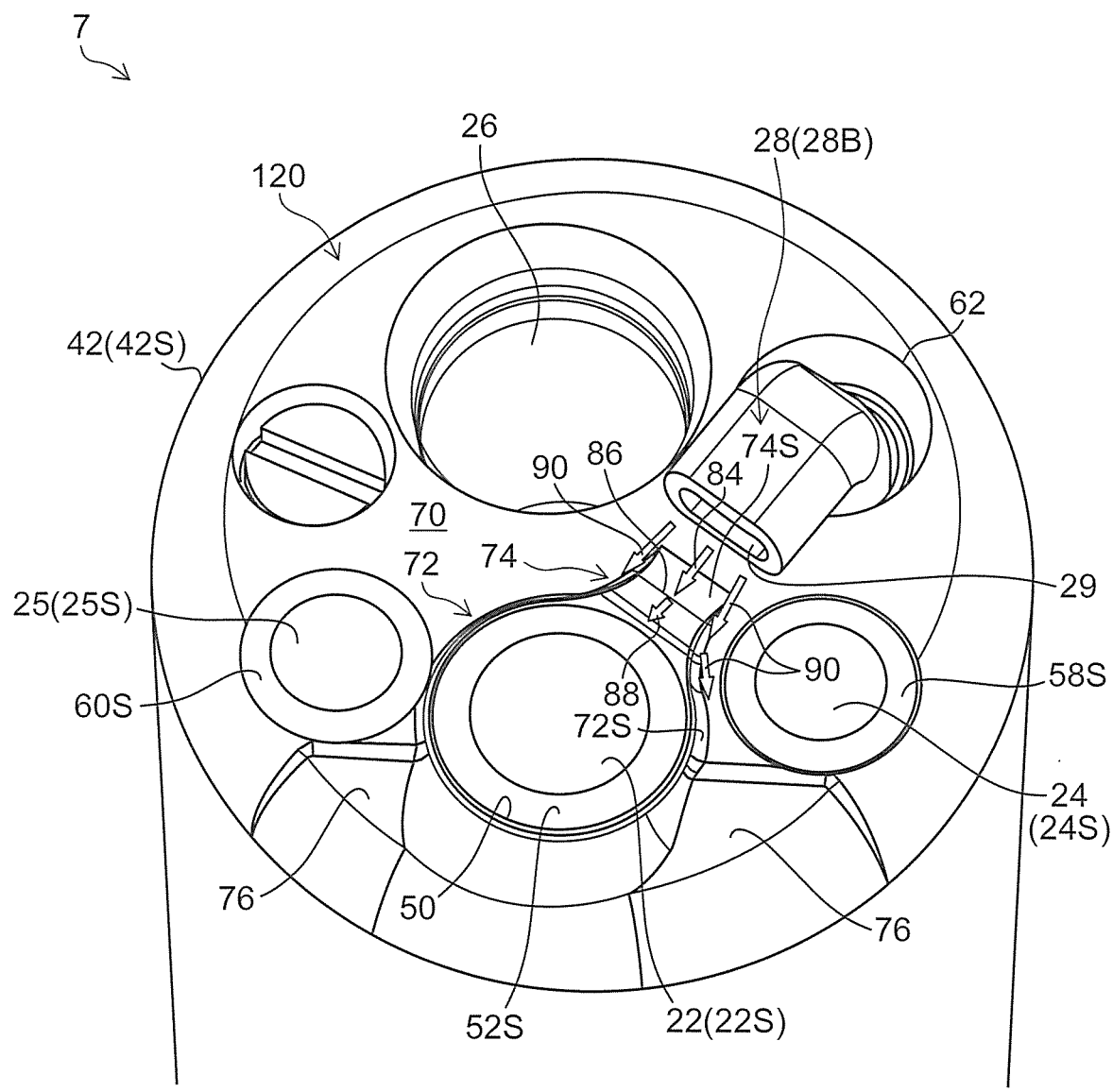
FIG. 7 is a perspective view of a distal end part including a distal end face of a third embodiment.

FIG. 7 is a perspective view of the distal end part 7 including a distal end face 120 of a third embodiment.

The stepped part 72 and the guide part 74 in the distal end face 120 of FIG. 7 have a structure similar to that of the stepped part 72 and the guide part 74 in the distal end face 100 of the second embodiment, and thus explanation thereof is omitted. There is a difference in that the width of the guide face 74S is larger than that of the second embodiment as a whole, to increase a flow rate of fluid guided to the surface 22S of the observation window 22 through the first fluid route 88 more than that of the second embodiment. In the case where the opening width of the fluid injection nozzle 28 is increased, the width of the guide face 74S may be increased as a whole accordingly, like the present embodiment.

In the present embodiment also, the width of the fluid guiding part 86 is less than the opening width of the injection port 29 of the fluid injection nozzle 28, as with the first embodiment.

Figure 8:
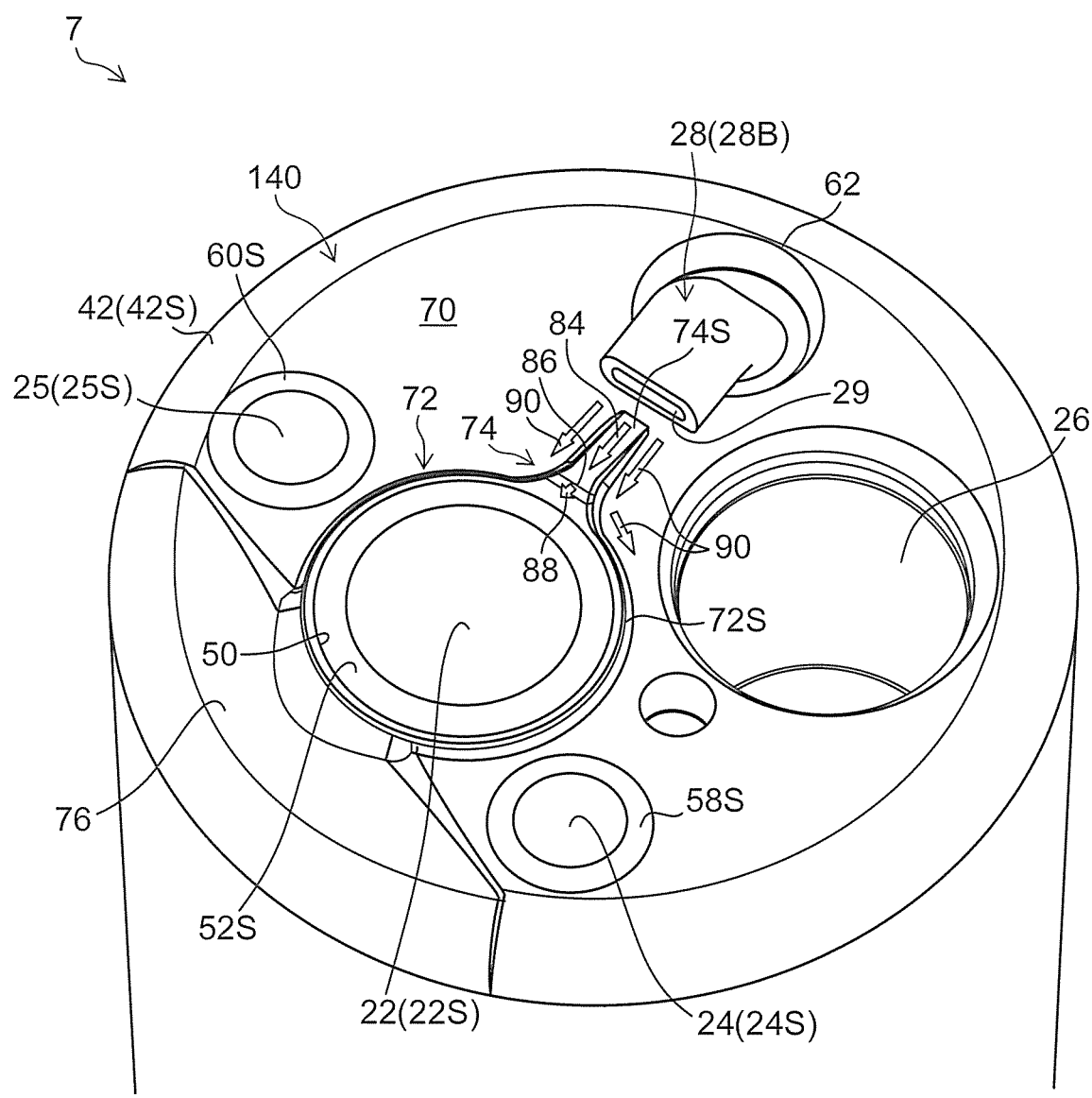
FIG. 8 is a perspective view of a distal end part including a distal end face of a fourth embodiment.

FIG. 8 is a perspective view of the distal end part 7 including a distal end face 140 of a fourth embodiment.

The distal end face 140 in FIG. 8, as with the distal end face 100 of the second embodiment, does not include the nozzle support part 80 as the stepped part 72 and the guide part 74, among the nozzle support part 80, the fluid initial passing part 84 including the proximal end route 82, the fluid guiding part 86, the first fluid route 88, and the second fluid route 90 in the distal end face 20 of the first embodiment. In addition, the fluid initial passing part 84 is greatly different from that in the distal end face 20 of the first embodiment.

That is, the guide part 74 is formed from a position separated from the injection port 29 of the fluid injection nozzle 28, and the guide face 74S of the guide part 74 is an inclined surface that is inclined to the distal end side in the longitudinal axial direction as a distance to the observation window 22 decreases.

The width of the guide face 74S has no narrowed part (constriction), and the guide face 74S is composed of a part having a constant width and a part having a width which increases toward the observation window 22.

Thus, the guide part 74 does not include the nozzle support part 80, and the distal end part 28B of the fluid injection nozzle 28 is arranged at a position where the distal end part 28B directly abuts on the reference plane 70 of the distal end cover 42.

A guide face of the fluid initial passing part 84 is composed of the guide face 74S of the guide part 74 from a position separated from the reference plane 70 which is perpendicular to the longitudinal axis and the injection port 29, the guide face 74S inclining to the distal end side in the longitudinal axial direction as a distance from the fluid injection nozzle 28 increases.

In addition, the fluid guiding part 86 is located at a position from which the width of the guide face 74S increases toward the observation window 22, and the width of the fluid guiding part 86 is less than the opening width of the injection port 29 of the fluid injection nozzle 28, as with the first embodiment.

A range from the fluid guiding part 86 to the guide face 74S of the guide part 74 on an observation window 22 side constitutes a guide face (first inclined surface) of the first fluid route 88, which inclines to the distal end side in the longitudinal axial direction from the fluid guiding part 86 toward the observation window 22.

In the case where opening width of the fluid injection nozzle 28 is reduced like the guide part 74 of the present embodiment, the guide face 74S may be reduced in width as a whole accordingly.

Figure 9:
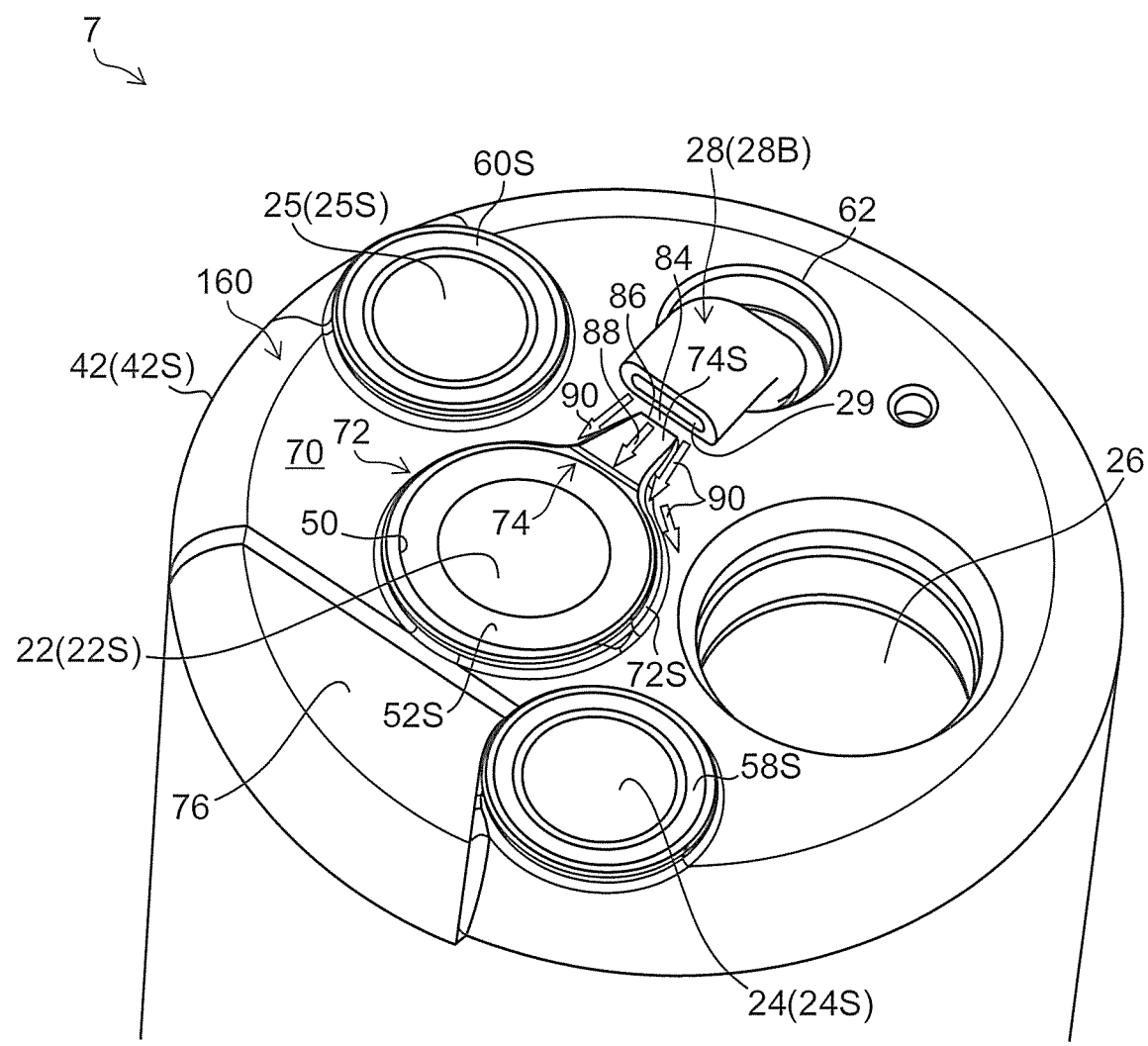
FIG. 9 is a perspective view of a distal end part including a distal end face of a fifth embodiment.
Figure 10:
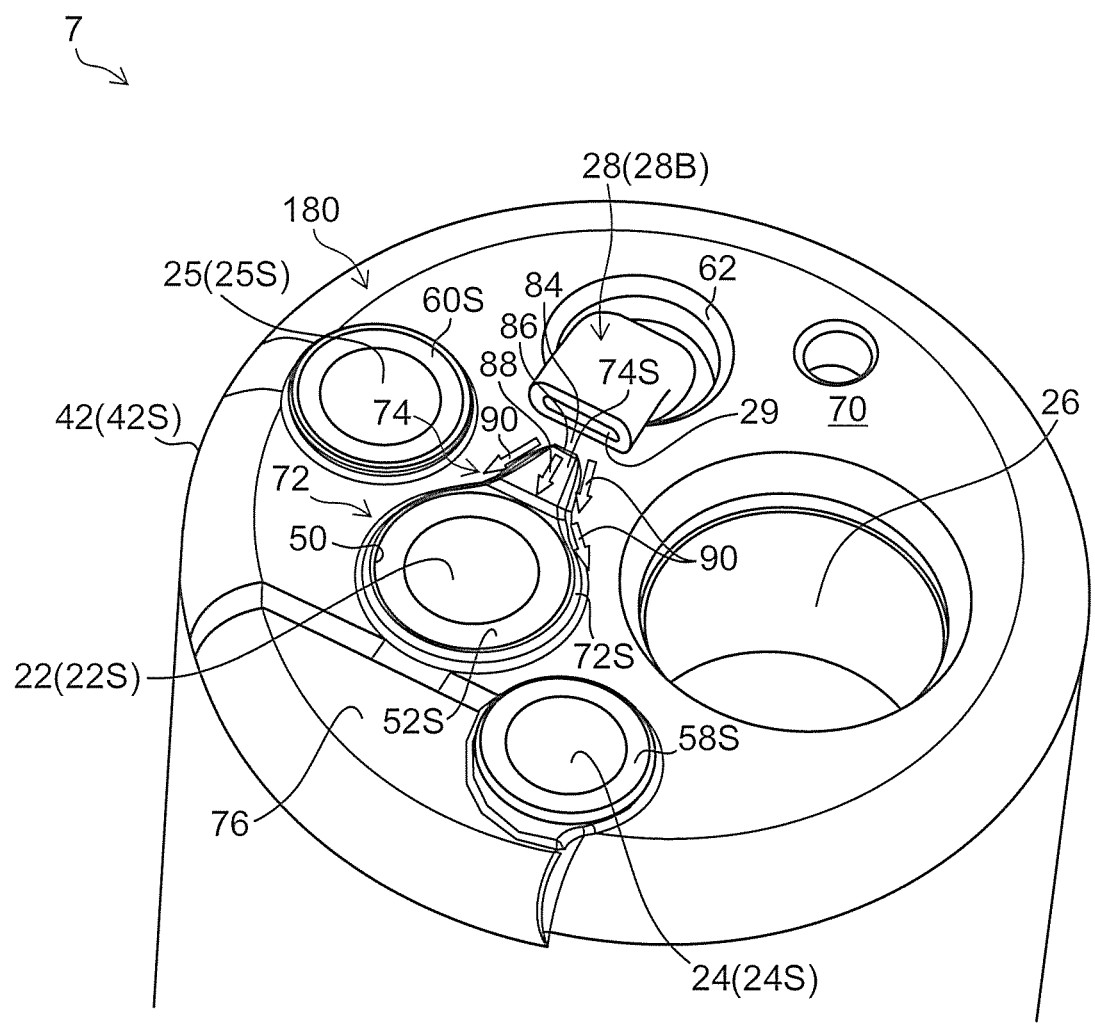
FIG. 10 is a perspective view of a distal end part including a distal end face of a sixth embodiment.

FIGS. 9 and 10 are perspective views of the distal end parts 7 including distal end faces 160 and 180 of fifth and sixth embodiments, respectively.

The distal end faces 160 and 180 in FIGS. 9 and 10 include the stepped parts 72 and the guide parts 74, with similar structure, and each of the guide parts 74 does not include the nozzle support part 80 and the fluid initial passing part 84, among the nozzle support part 80, the fluid initial passing part 84 including the proximal end route 82, the fluid guiding part 86, the first fluid route 88 and the second fluid route 90 in the distal end face 20 of the first embodiment.

That is, the guide part 74 is formed from a position separated from the injection port 29 of the fluid injection nozzle 28, and the guide face 74S of the guide part 74 is an inclined surface that is inclined to the distal end side in the longitudinal axial direction as a distance to the observation window 22 decreases.

The width of the guide face 74S has no narrowed part (constriction), and the guide face 74S is composed of only a part having a width which increases toward the observation window 22.

Thus, the guide part 74 does not include the nozzle support part 80, and the distal end part 28B of the fluid injection nozzle 28 is arranged at a position where the distal end part 28B directly abuts on the reference plane 70 of the distal end cover 42.

A guide face of the fluid initial passing part 84 is composed of only the reference plane 70 which is perpendicular to the longitudinal axis. That is, the guide part 74 does not include the fluid initial passing part 84. In the case where the distance between the fluid injection nozzle 28 and the observation window 22 is reduced, a form not only without the nozzle support part 80, but also without the fluid initial passing part 84, like the guide part 74 of the present embodiment, may be adopted.

The fluid guiding part 86 is an edge part of the guide face 74S, which is closest to the fluid injection nozzle 28. A width of the fluid guiding part 86 is less than the opening width of the injection port 29 of the fluid injection nozzle 28, as with the first embodiment.

A range from the fluid guiding part 86 to the guide face 74S of the guide part 74 on an observation window 22 side, or the whole of the guide face 74S of the guide part 74, constitutes a guide face (first inclined surface) of the first fluid route 88, which inclines to the distal end side in the longitudinal axial direction from the fluid guiding part 86 toward the observation window 22.

A diameter of the surface 22S of the observation window 22 in the distal end face 180 of the sixth embodiment of FIG. 10 is smaller than that of the distal end face 160 of the fifth embodiment of FIG. 9, and accordingly a width of the guide face 74S of the guide part 74 in the distal end face 180 is also less than that in the distal end face 160, as a whole.

What is claimed is:

1. An endoscope comprising:
    an insertion section having a distal end, a proximal end, and a longitudinal axis;
    an operation section provided at the proximal end of the insertion section;
    a distal end face provided at the distal end of the insertion section;
    an observation window arranged in the distal end face;
    a fluid injection nozzle arranged in the distal end face, the fluid injection nozzle configured to inject a fluid to the observation window;
    a stepped part that projects distally from the distal end face by a first height in a direction of the longitudinal axis and surrounds a circumference of the observation window, wherein the stepped part includes a stepped face that extends from the distal end face to the circumference of the observation window;
    a guide part that projects distally from the distal end face by a second height in the direction of the longitudinal axis, connects with the stepped part and extends continuously between the fluid injection nozzle and the observation window, wherein the guide part includes a guide face that is orthogonal to the longitudinal axis and a pair of side faces that are located on both sides of the guide face and connect with the stepped face, and the second height is greater than the first height;
    a fluid guiding part that projects distally from the distal end face by a third height in the direction of the longitudinal axis, is provided at a position between the fluid injection nozzle and the observation window and connects between a first guide face and a third guide face of the endoscope, wherein the fluid guiding part has a width less than an opening width of the fluid injection nozzle in a direction orthogonal to a straight line connecting a center of the fluid injection nozzle and a center of the observation window, the fluid guiding part is configured to guide a first portion of the fluid injected from an injection port of the fluid injection nozzle that flows through the guide part to an observation window side, and the third height is greater than or equal to the first height;
    a first fluid route having the first guide face configured to guide the first portion of the fluid guided by the fluid guiding part to the observation window, the first guide face being formed of a continuous surface connecting between the fluid guiding part and the observation window and having the third height; and
    a second fluid route having a second guide face configured to guide a second portion of the fluid deviated from the first portion of the fluid guided by the fluid guiding part to a region adjacent to the observation window, the second guide face being formed of a portion of the stepped face that is adjacent to the fluid guiding part and a portion of each of the side faces that is located beside the first guide face, such that the second guide face is wider on the observation window side than on a fluid injection nozzle side, and the second guide face having a component obliquely intersecting with the straight line connecting the center of the fluid injection nozzle and the center of the observation window when the distal end face is viewed from a front in the direction of the longitudinal axis,
    wherein the third guide face is formed of a portion of the guide part that is adjacent to the injection port and provided between the fluid injection nozzle and the fluid guiding part, and the third guide face includes a first surface connected between the injection port and the continuous surface of the first guide face and having the second height, wherein the second height gradually and continuously decreases from below the injection port at the fluid injection nozzle side towards the fluid guiding part, and the second height is greater than the third height,
    wherein the guide face of the guide part extends from the fluid injection nozzle, through the fluid guiding part, to the observation window, so that the first portion of the fluid injected from the injection port of fluid injection nozzle is straightforwardly guided from the fluid injection nozzle side to the observation window side.

2. The endoscope according to claim 1, wherein the distal end face includes a fluid holding region in the region adjacent to the observation window.

3. The endoscope according to claim 2, wherein the fluid holding region has a surface energy higher than a surface energy of a surface of the observation window.

4. The endoscope according to claim 2, wherein the distal end face includes a recessed part in the region adjacent to the observation window, and the recessed part constitutes the fluid holding region.

5. An endoscope comprising:
    an insertion section having a distal end, a proximal end, and a longitudinal axis;
    an operation section provided at the proximal end of the insertion section;
    a distal end face provided at the distal end of the insertion section;
    an observation window arranged in the distal end face;
    a fluid injection nozzle arranged in the distal end face, the fluid injection nozzle configured to inject a fluid to the observation window;
    a stepped part that projects distally from the distal end face by a first height in a direction of the longitudinal axis and surrounds a circumference of the observation window, wherein the stepped part includes a stepped face that extends from the distal end face to the circumference of the observation window;
    a guide part that projects distally from the distal end face by a second height in the direction of the longitudinal axis, connects with the stepped part and extends continuously between the fluid injection nozzle and the observation window, wherein the guide part includes a guide face that is orthogonal to the longitudinal axis and a pair of side faces that are located on both sides of the guide face and connect with the stepped face, and the second height is greater than the first height;
    a fluid guiding part that projects distally from the distal end face by a third height in the direction of the longitudinal axis, is provided at a position between the fluid injection nozzle and the observation window and connects between a first guide face and a third guide face of the endoscope, wherein the fluid guiding part has a width less than an opening width of the fluid injection nozzle in a direction orthogonal to a straight line connecting a center of the fluid injection nozzle and a center of the observation window, the fluid guiding part is configured to guide a first portion of the fluid injected from an injection port of the fluid injection nozzle that flows through the guide part to an observation window side, and the third height is greater than or equal to the first height;

a first fluid route having the first guide face configured to guide the first portion of the fluid guided by the fluid guiding part to the observation window, the first guide face being formed of a continuous surface connecting between the fluid guiding part and the observation window and having the third height; and a second fluid route having a second guide face configured to guide a second portion of the fluid deviated from the first portion of the fluid guided by the fluid guiding part to a region adjacent to the observation window, the second guide face being formed of a portion of the stepped face that is adjacent to the fluid guiding part and a portion of each of the side faces that is located beside the first guide face, such that the second guide face is wider on the observation window side than on a fluid injection nozzle side, and the second guide face having a component obliquely intersecting with the straight line connecting the center of the fluid injection nozzle and the center of the observation window when the distal end face is viewed from a front in the direction of the longitudinal axis, wherein the third guide face is formed of a portion of the guide part that is adjacent to the injection port and provided between the fluid injection nozzle and the fluid guiding part, and the third guide face includes a first surface connected between the injection port and the continuous surface of the first guide face and having the second height, wherein the second height gradually and continuously decreases from below the injection port at the fluid injection nozzle side towards the fluid guiding part, and the second height is greater than the third height, wherein the guide face of the guide part extends from the fluid injection nozzle, through the fluid guiding part, to the observation window, so that the first portion of the fluid injected from the injection port of fluid injection nozzle is straightforwardly guided from the fluid injection nozzle side to the observation window side, when it is assumed that the straight line connecting the center of the fluid injection nozzle and the center of the observation window is a first straight line, and a line in a plane orthogonal to the first straight line and being orthogonal to an optical axis of the observation window is a second straight line, the first guide face is composed of only a face parallel to the plane containing the second straight line.

\* \* \* \* \*